(12) United States Patent
Rudischhauser et al.

(10) Patent No.: US 8,029,437 B2
(45) Date of Patent: Oct. 4, 2011

(54) ENDOSCOPE AND METHOD FOR ASSEMBLING COMPONENTS OF AN OPTICAL SYSTEM

(75) Inventors: Jürgen Rudischhauser, Tuttlingen (DE); Klaus Renner, Liptingen (DE); Markus Kupferschmid, Emmingen-Liptingen (DE)

(73) Assignee: Karl Storz GmbH & Co. KG (DE)

( * ) Notice: Subject to any disclaimer, the term of this patent is extended or adjusted under 35 U.S.C. 154(b) by 253 days.

(21) Appl. No.: 12/413,891

(22) Filed: Mar. 30, 2009

(65) Prior Publication Data

US 2009/0182199 A1 Jul. 16, 2009

Related U.S. Application Data

(60) Division of application No. 11/206,562, filed on Aug. 18, 2005, now Pat. No. 7,530,945, which is a continuation of application No. PCT/EP2004/000765, filed on Jan. 29, 2004.

(51) Int. Cl.
*A61B 1/00* (2006.01)

(52) U.S. Cl. ........ 600/138; 600/121; 600/130; 600/139; 600/160; 600/161; 359/434; 359/435; 359/849

(58) Field of Classification Search .................. 600/121, 600/128, 130, 138–139, 160, 182; 359/434–435, 359/894

See application file for complete search history.

(56) References Cited

U.S. PATENT DOCUMENTS

| | | | |
|---|---|---|---|
| 3,730,175 A * | 5/1973 | Fukami et al. ................ 600/176 |
| 4,148,550 A | 4/1979 | MacAnally |
| 4,148,551 A | 4/1979 | MacAnally |
| 4,750,476 A | 6/1988 | Forkner et al. |
| 4,822,154 A | 4/1989 | Oxford et al. |
| 4,966,439 A | 10/1990 | Althaus et al. |
| 5,419,313 A | 5/1995 | Lemke |
| 5,452,395 A * | 9/1995 | Schichman et al. .......... 385/125 |
| 5,480,302 A | 1/1996 | Fife |
| 5,486,171 A * | 1/1996 | Chou .............................. 606/16 |
| 5,638,483 A * | 6/1997 | Konwitz ........................ 385/38 |
| 6,013,047 A * | 1/2000 | King .............................. 604/22 |
| 6,201,649 B1 | 3/2001 | Rudischhauser et al. |
| 6,305,536 B1 | 10/2001 | Tanaka |
| 6,366,726 B1 * | 4/2002 | Wach et al. ................... 385/115 |
| 6,398,723 B1 | 6/2002 | Kehr et al. |
| 6,471,640 B1 | 10/2002 | Frische et al. |
| 7,385,772 B2 | 6/2008 | Forkey et al. |
| 7,595,935 B2 * | 9/2009 | Lei et al. ....................... 359/665 |
| 2001/0034514 A1 * | 10/2001 | Parker ........................... 604/525 |
| 2002/0007111 A1 | 1/2002 | Deckert et al. |

FOREIGN PATENT DOCUMENTS

DE     2812369 A1     11/1978

(Continued)

OTHER PUBLICATIONS

International Search Report, May 13, 2004, 7 pages.

*Primary Examiner* — Matthew J Kasztejna
(74) *Attorney, Agent, or Firm* — St. Onge Steward Johnston & Reens LLC

(57) ABSTRACT

An endoscope has a tubular shaft whose interior contains components, in particular lenses, spacers, diaphragms, prisms and filters of an optical system, said components being at least partially surrounded by a support piece made of shrunk material. It is proposed that the components be surrounded by a transparent and tube-sleeve-shaped shrunk material which has been shrunk before the components are introduced into the tubular shaft.

14 Claims, 3 Drawing Sheets

FOREIGN PATENT DOCUMENTS

| | | |
|---|---|---|
| DE | 3738451 A1 | 5/1988 |
| DE | 3912720 A1 | 10/1990 |
| DE | 19732991 A1 | 2/1999 |
| DE | 19912656 A1 | 11/2000 |
| DE | 10253559 A1 | 6/2004 |
| EP | 0337142 A1 | 10/1989 |

* cited by examiner

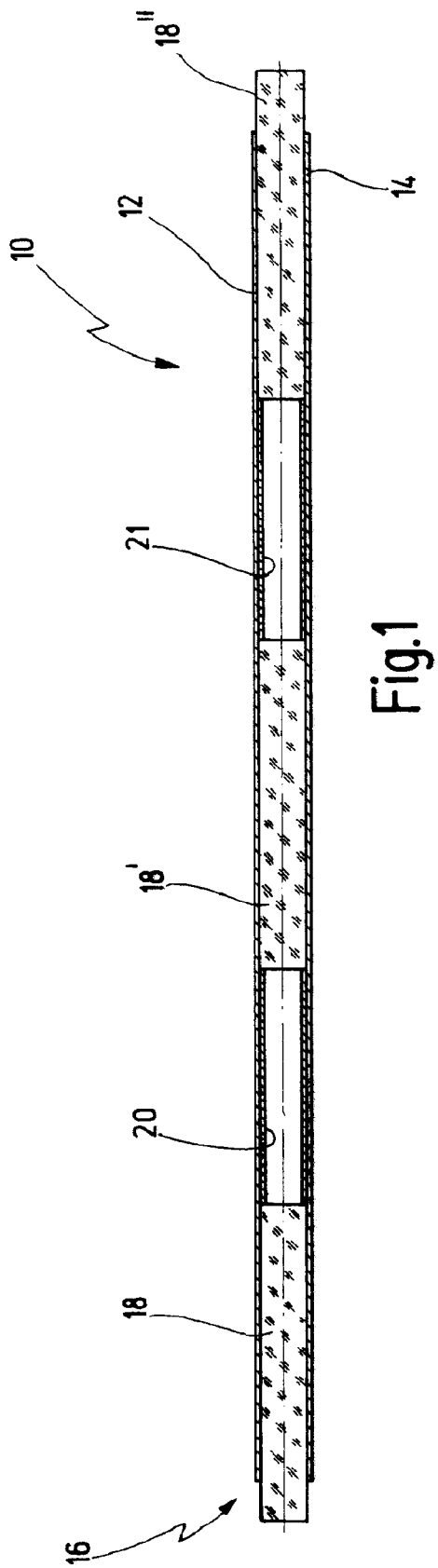
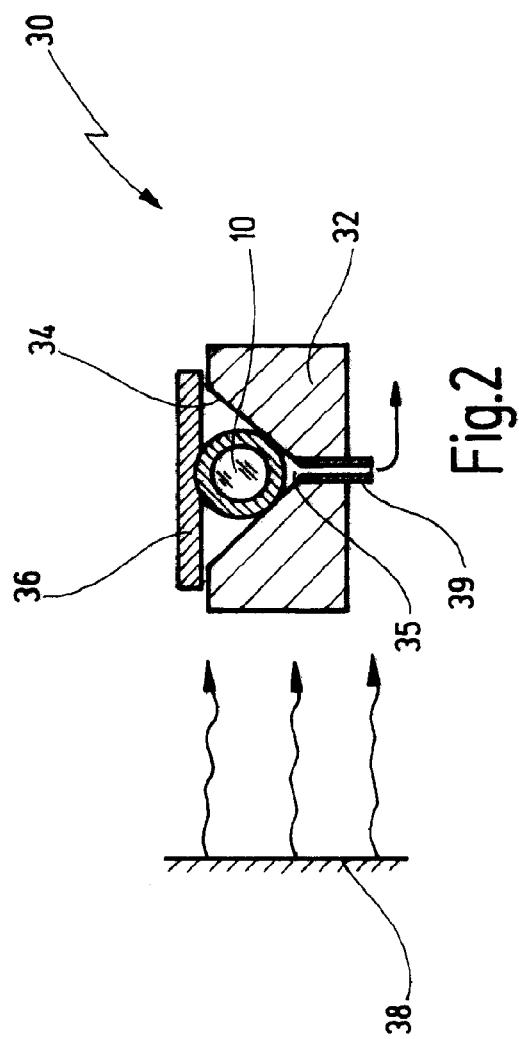
Fig.1
Fig.2

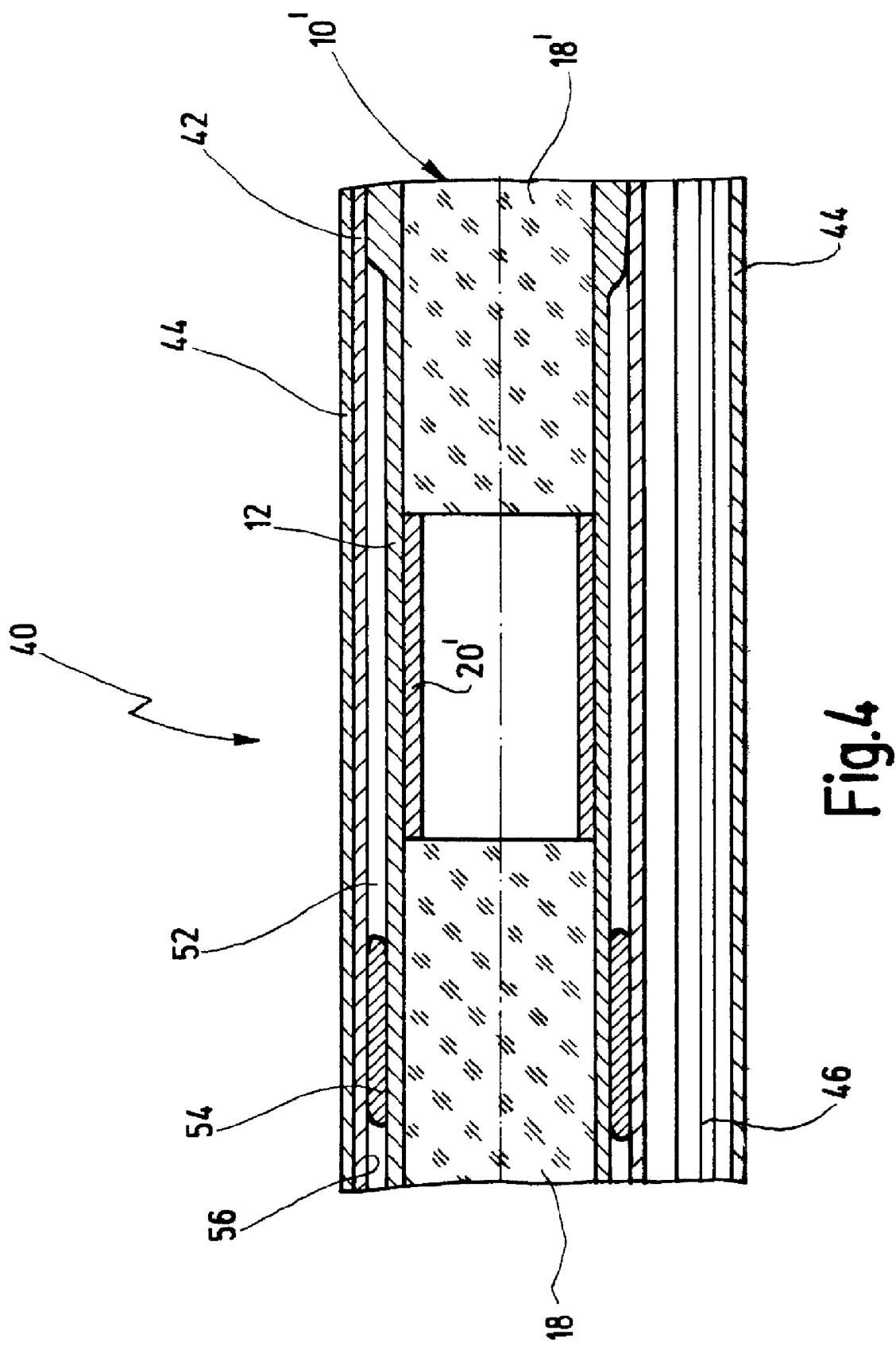

ENDOSCOPE AND METHOD FOR ASSEMBLING COMPONENTS OF AN OPTICAL SYSTEM

CROSS-REFERENCE TO RELATED APPLICATIONS

This application is a division of U.S. patent application Ser. No. 11/206,562 filed Aug. 18, 2005, now U.S. Pat. No. 7,530,945 which in turn is a continuation of international application PCT/EP 2004/000765 filed on Jan. 29, 2004 which designates the United States and which claims priority of German patent application No. 103 07 904.1 filed on Feb. 18, 2003. All prior applications are herein incorporated by reference.

BACKGROUND OF THE INVENTION

The invention relates to an endoscope, with a tubular shaft whose interior contains components, in particular lenses, spacers, diaphragms, prisms and filters of an optical system, said components being at least partially surrounded by a support piece made of shrunk material.

The invention also relates to a method for assembling components, in particular lenses, spacers, diaphragms and filters of an optical system in the interior of a tubular shaft of an endoscope, said components being surrounded by a support piece made of shrunk material.

Such an endoscope and such a method are known from document DE 197 32 991 C2.

In the method disclosed in the latter document, the shrinkable material is used to fix the components of the optical system in the tubular shaft. To do this, the components are introduced into a support piece made of shrinkable material at least partially surrounding said components, and this unit is then pushed into the tubular shaft. The dimensions are such that a small gap remains between the outside face of the support piece and the inside face of the tubular shaft. As the material shrinks, it expands slightly in the radial direction and fills the gap, so that in this way the unit is fixed on the inside face of the tubular shaft.

DE 39 12 720 C2 also discloses the use of a plastic shrinkable tube for positioning the elements of a relay lens system of an endoscope. The material is chosen such that it does not transmit light, i.e. is opaque. This is intended to ensure that light does not pass from the light guide into the area of the relay lens system or into the area of the objective lens and there cause reflections or glare. The lenses of the lens system can first be placed in a correct position. The shrinkable tube is then shrunk by application of heat so that it holds the lenses, without a lens fixture in the conventional sense being needed.

This construction is intended to make it possible to produce endoscopes extremely inexpensively, and provision is therefore also made to produce the lenses from plastic.

In the document DE 39 12 720 C2 mentioned earlier, the aim is to fix the expensive components of the optical system to the inside face of a metal tubular shaft by using the shrink properties of the material surrounding these components.

It is an object of the present invention is to further optimize an endoscope and a method for assembling components in such a way that, by using shrinkable materials, it is possible to fix the optical components relative to one another in a way which can also be checked.

SUMMARY OF THE INVENTION

According to the invention, the object in respect of an endoscope is achieved by the fact that the components are surrounded by a transparent and tube-shaped shrunk material which has been shrunk before the components are introduced into the tubular shaft.

According to the invention, the object in respect of a method is achieved by the following steps, namely introducing the components into a transparent and tube-shaped shrinkable material to form a unit, shrinking the material to fix the position of the components relative to one another, checking the position of the components relative to one another through the transparent shrunk material, and introducing the unit composed of shrunk tube-shaped material, and the components contained therein, into the tubular shaft.

The optical system of an endoscope is made up of a succession of different optical components. A particularly good image quality can be obtained using what are referred to as rod lenses. For this purpose, several rod lenses separated from one another by spacers are arranged in series, and other components such as diaphragms, filters or cover glasses or prisms can additionally be provided.

For a good image quality, it is not only necessary for these parts to be precisely oriented relative to one another and fixed axially along an optical axis; it is also necessary for their relative rotation positions to be unchangeable. In the course of assembly, it is expedient to check the optical image qualities of such a lens system so that, if appropriate, systems with optical misalignments can be eliminated.

The quality check of the optical system is normally made only after complete assembly of the endoscope. If optical errors are found, it is then very expensive to correct these, and in most cases the endoscope has to be completely dismantled.

With the present invention, it is now possible to produce a unit composed of the optical components and the tube outside the endoscope and to check this unit visually. For this purpose, a transparent shrinkable material is used which in many respects affords advantages over the opaque materials known from the prior art. On the one hand, the position of the components relative to one another can be visually checked at the time the individual components are introduced into the material before it has been shrunk. In particular, it is possible to establish whether, for example, individual filter components or diaphragms have turned relative to one another, or whether, for example, a gap is or is not present between a spacer and a rod lens.

It is also possible to check the correct arrangement of the lens components, lenses, spacers and, if appropriate, diaphragms, filters and/or prisms.

After this unit has been shrunk, a check can once again be made, namely as to whether the shrinking has caused any relative changes to take place. During shrinkage, the material surrounding the optical elements moves. By provision of the transparent material, it is now possible for the first time to perform a visual check even after the shrinking process. Of course, checks are also already possible in the direction of the optical axis that is to say through the optical elements. Thus, such a preliminary check can be made even before the optical system is fitted in the shaft. After introduction of the shrunk unit and final positioning of this unit in the shaft, a final check can then also be made.

In this way, the reliability of the assembly and the assembly as such, can also be simplified and improved.

In a further embodiment of the invention, all the components are surrounded by a single tube of transparent and shrunk material.

This measure has the advantage that all the components are introduced into a single tube-shaped body and this unit can be handled as such after shrinking, for example can be simply inserted as a unit into the tubular shaft of the endoscope. This unit can be introduced into the endoscope shaft in the appropriate position of rotation or can be brought to the correct position of rotation after introduction. If, for example, a front closure forms a prism with a lateral angle of view, the position, that is to say lateral angle of view, can be chosen to the left, to the right, upward or downward.

In a further embodiment of the invention, the components are fixed to the inside face of the tubular shaft via the tube-shaped shrunk material.

There are a great many ways of doing this, for example by adhesive fixation where the adhesive can be applied before introduction of the unit, or can be introduced for fixing after introduction through radial bores in the tubular shaft.

In a further embodiment of the invention, the tube is fixed to the inside face of the tubular shaft by radial expansion of the shrunk material.

This measure has the advantage that the effect, known from DE 197 32 991 C2, can now additionally be used to fix the already "pre-shrunk" unit to the inside face of the tubular shaft by a further shrinking process. This entails a further axial shrinkage with slight radial expansion.

The extent of the shrinking process can be controlled by the nature and duration of the shrink treatment. In a first preliminary shrinking process, the shrink phenomenon is utilized so that the components introduced into the tube can be fixed relative to one another. After insertion of this unit into the tubular shaft, a further shrinking process is carried out, its sole purpose being to fill the gap between the outside face of the unit, composed of pre-shrunk shrinkable tube and the components contained therein, and the inside face of the tubular shaft into which this unit is inserted, in order thereby to fix this unit on this inside face of the tubular shaft as it experiences a slight expansion in the radial direction during this further shrinking. For this purpose, certain preliminary treatments of the shrinkable tube can be envisaged, for example one or more beads in the form of rings or partial rings lying within the cross section. These geometric departures from the otherwise cylindrical shape of the shrinkable tube entail radial expansion of the geometry of the shrinkable tube upon its axial shrinkage, without expansion of the material as such.

In one embodiment of the method, the unit composed of components and of transparent shrinkable material is inserted, before shrinkage, into a retaining device in which the unit lies in an oriented position.

This measure has the advantage that the retaining device can provide additional measures for keeping the unit correctly aligned. It is also possible, after insertion in the retaining device, to check the unit for correct fit before the shrink process is instigated.

The unit inserted in the retaining device can be additionally fixed by a partial vacuum.

In a further embodiment of the method, the unit is inserted into a groove of the retaining device.

This is particularly advantageous if long endoscope shafts are to be fitted and in particular if there is a risk of the force of gravity causing bending or bulging.

In a further embodiment, the unit inserted into the retaining device is weighed down by application of an object.

This measure has the advantage that not only is a support provided in the direction of gravity by way of insertion, but bending in the sense of lifting up can be prevented by application of the object before shrinkage.

In a further embodiment, the object is applied with a partial form fit onto the unit.

This measure is of advantage if a great many small individual parts are assembled which have a tendency to change their position in the event of movements, for example during shrinkage.

It will be appreciated that the features mentioned above and those still to be explained below can be used not only in the respectively cited combination, but also in other combinations or singly, without departing from the scope of the present invention.

BRIEF DESCRIPTION OF THE DRAWINGS

The invention is described and explained in greater detail below on the basis of a number of selected illustrative embodiments and with reference to the attached drawings, in which:

FIG. 1 shows a longitudinal section through a unit composed of a tube of transparent and shrinkable material and of optical components, namely rod lenses and spacers, before shrinkage, FIG. 2 shows a cross section of a retaining device in which the unit shown in FIG. 1 is inserted, specifically upon shrinkage, FIG. 4 shows, on a greatly enlarged scale, a partial longitudinal section through a shaft of an endoscope in whose tubular shaft a unit according to the invention is inserted, the left-hand half showing the unit fixed on the inside face of the tubular shaft by adhesive contacts, and the right-hand side showing it being fixed by means of further shrinkage.

DETAILED DESCRIPTION OF THE INVENTION

Figure 3:
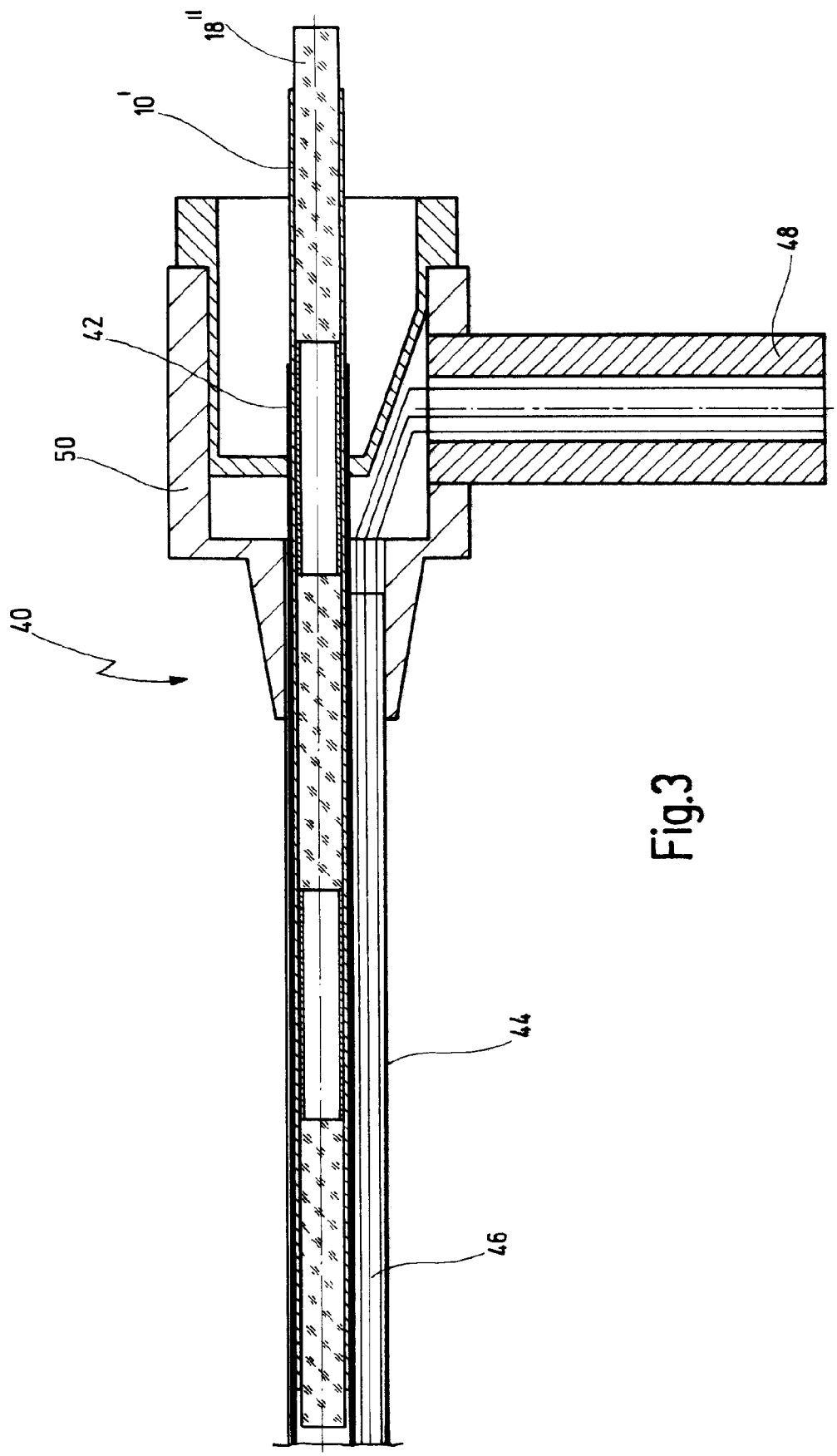
FIG. 3 shows a longitudinal section through an endoscope during assembly, into which endoscope the unit shown in FIG. 1, after it has been shrunk in the retaining device 3 shown in FIG. 2, is inserted into the tubular shaft.

In FIG. 1, a unit, designated in its entirety by reference number 10, comprises a tube 12 made of transparent and shrinkable material 14. A plurality of components 16 of an optical system are introduced into the tube 12, specifically, as viewed from left to right, a rod lens 18, whose external diameter corresponds approximately to the clear internal diameter of the tube 12, a tubular and stiff spacer 20, a further rod lens 18', a further spacer 21, and a further rod lens 18".

This unit 10 is shown only by way of example, and other components such as filters, diaphragms or the like can of course also be included. It is also possible to provide closure windows at the ends or, in the case of an angled side view, suitable prisms.

By virtue of the transparency of the material 14, it is possible to check the desired correct fit of these components 16 relative to one another from the outside, for example to check whether the opposing end faces of the two rod lenses 18 and 18' bear exactly on the spacer 20.

For the shrinking process, the unit 10 is inserted into a retaining device 30, as is shown in FIG. 2.

The retaining device 30 has an elongate body 32 whose length corresponds to least to the length of the unit 10.

Cut out on the top face of the body 32 there is a longitudinally extending groove 34 which is configured in such a way that the unit 10 can be inserted into this groove, the unit 10 protruding slightly above the upper edge of the retaining device.

A roughly plate-shaped object 36 is placed onto this protruding area and bears with an at least partial form fit on the top face of the unit 10, as it were pressing said unit 10 into the groove 34.

In this way, the unit 10 is inserted and fixed in the retaining device 30 in such a way that a uniform shrinking of the material 14 of the tube 12 is possible, but with the unit still being fixed in position.

Alternatively or in addition, the position can be fixed by use of a partial vacuum. For this purpose, at least one opening 35 is provided in the bottom of the groove 34 and can be connected via an attachment piece 39 to a partial vacuum source (not shown here).

As is known per se, in the actual shrinking process, energy is supplied from an energy source 38 and causes the material 14 of the tube 12 to shrink.

One energy source is, for example, heat, if the material is designed such that it shrinks when heated. It is of course also possible to heat the retaining device 30 itself or to cause heated fluid to flow onto the retaining device.

After the shrinkage, the object 36 is taken off and the now shrunk unit 10' is removed from the retaining device 30.

By virtue of the transparency of the material 14 which is still present even after the shrinkage, it is possible once again to check, from the outside, the correct fit of the individual components 16 relative to one another.

The shrunk unit 10' is then inserted into a tubular shaft 42 of an endoscope 40, as is shown in FIG. 3.

The endoscope 40 shown in FIG. 3 is represented highly schematically and, in addition to the tubular shaft 42 also referred to as inner tube, it also comprises an outer tube 44 of greater diameter which is mounted in a housing 50. The tubular shaft 42 is received in the interior of the outer tube 44.

As is normally the case, a light guide 46 is arranged in an approximately crescent-shaped space between tubular shaft 42 and outer tube 44, said light guide 46 leading to a laterally angled light guide attachment 48. In the illustrative embodiment shown, the light guide 46 is composed of a bundle of light-conducting glass fibers. The state shown in FIG. 3 is a state of partial assembly in which the eyepiece cup is still to be applied to the right-hand end, and, if appropriate, closure components or the like to the left-hand end.

FIG. 4 shows a cross section, on a greatly enlarged scale, through the shaft of an endoscope 40, and, for the sake of clarity of the drawing, a slightly shorter spacer 20' is shown here separating the two rod lenses 18 and 18' from one another.

From the cross-sectional view in FIG. 4 it will be evident that the unit 10' is inserted after shrinkage into the tubular shaft 42 received in the outer tube 44. The external diameter is chosen in such a way that a small gap 52 is present between the outside face of the shrunk tube 12 and the inside face 56 of the tubular shaft 42.

In FIG. 4, for the sake of clarity of the drawing, this gap 52 is shown much larger than it really is.

The width of the gap is chosen such that the shrunk unit 10' can be pushed into the tubular shaft 42 easily, or at any rate with minimal resistance.

FIG. 4 shows, on the left-hand side, that the unit 10' is fixed on the inside face 56 of the tubular shaft 42 via an adhesive 54. The adhesive 54 can either be introduced through openings (not shown here) from the outside or can be applied to the shrunk unit 10' before the latter is inserted into the tubular shaft 42.

The right-hand end of FIG. 4 shows that the unit 10' is fixed to the inside face 56 of the tubular shaft 52 by further shrinkage of the tube and associated radial expansion, in which case, as has already been mentioned, the shrinkable tube can be geometrically designed in such a way that, for example by provision of beads, incisions or other configurations which promote expansion at predetermined locations, this expansion takes place in a specific manner during the further shrinking process.

This possibility is chosen when the material 14 of the tube 12 permits two shrinking processes, namely a first or preliminary shrinking process for fixing the components to one another, for example in the retaining device 30 shown in FIG. 2, and then, after insertion into the tubular shaft 42 as shown in FIG. 4, a further shrinking and radial expansion for filling the gap 52.

What is claimed is:

1. An endoscope, comprising:
   a tubular shaft, having an inside face,
   an optical system having several components, said components of said optical system are contained in an interior of said tubular shaft,
   said components comprising at least two of the following: a lens, a spacer, a diaphragm, a prism and a filter, said components directly surrounded by a support piece made of a shrunk material, wherein
   said shrunk material is a transparent material,
   said support piece made of said transparent material has a shape of a tube, and
   said tube containing said components of said optical system has been shrunk prior to inserting said tube into said interior of said tubular shaft, for allowing a visual check of a position of said components relative to one another, and
   a gap located between an outside surface of said tube of shrunk material and said inside face of said tubular shaft.

2. The endoscope of claim 1, wherein said components are surrounded by a single tube made of said transparent material.

3. The endoscope of claim 1, wherein said shrunk transparent tube containing said components is fixed to the inside face of said tubular shaft.

4. The endoscope of claim 3, wherein said tube being fixed to said inside face of said tubular shaft by a radial expansion of said shrunk material.

5. The endoscope of claim 4, wherein said shrunk tube containing said components has in at least one area a configuration effecting a radial expansion during an axial shrinkage of said tube already inserted into said hollow shaft.

6. The endoscope of claim 5, wherein said configuration being at least one of thickened parts, beads and incisions of said transparent material.

7. The endoscope of claim 1, wherein said components comprise at least one of each of the following: a lens, a spacer, a diaphragm, a prism and a filter.

8. An endoscope, comprising:
   a tubular shaft having an interior and an inside face;
   an optical system including a plurality of components positioned in the interior of said shaft, the plurality of components comprising at least two of the following: a lens, a spacer, a diaphragm, a prism and a filter;
   a support piece comprising a shrunk material enclosing said optical system to fit into the interior of said tubular shaft and providing support for said optical system, said shrunk material directly surrounding said plurality of components;
   wherein said optical system is enclosed by and in contact with said shrunk material prior to insertion into said interior of said tubular shaft; and
   wherein said shrunk material is either transparent or translucent such that visual inspection of said plurality of components relative to each other may be conducted prior to insertion into said interior of said tubular shaft, and a gap located between an outside surface of said tube of shrunk material and said inside face of said tubular shaft.

9. The endoscope of claim 8, wherein said plurality of components is surrounded by a single tube made of said transparent or translucent material.

10. The endoscope of claim 8, wherein said shrunk transparent or translucent material containing said plurality of components is affixed to the inside face of said tubular shaft.

11. The endoscope of claim 10, wherein said shrunk transparent or translucent material is affixed to said inside face of said tubular shaft by a radial expansion of said shrunk transparent or translucent material.

12. The endoscope of claim 11, wherein said shrunk transparent or translucent material containing said plurality of components has in at least one area a configuration effecting a radial expansion during an axial shrinkage of said transparent or translucent material already inserted into the interior of said tubular shaft.

13. The endoscope of claim 11, wherein said configuration being at least one of thickened parts, beads and incisions of said transparent or translucent material.

14. The endoscope of claim 8, wherein said plurality of components comprise at least one of each of the following: a lens, a spacer, a diaphragm, a prism and a filter.

* * * * *